US009051542B2

(12) United States Patent
Wright et al.

(10) Patent No.: US 9,051,542 B2
(45) Date of Patent: Jun. 9, 2015

(54) COMPOSITIONS AND METHODS TO PREVENT AAV VECTOR AGGREGATION

(75) Inventors: John Fraser Wright, Princeton, NJ (US); Guang Qu, Alameda, CA (US)

(73) Assignee: Genzyme Corporation, Framingham, MA (US)

( * ) Notice: Subject to any disclaimer, the term of this patent is extended or adjusted under 35 U.S.C. 154(b) by 0 days.

(21) Appl. No.: 12/661,553

(22) Filed: Mar. 19, 2010

(65) Prior Publication Data

US 2011/0076744 A1  Mar. 31, 2011

Related U.S. Application Data

(63) Continuation of application No. 11/141,996, filed on Jun. 1, 2005, now Pat. No. 7,704,721.

(60) Provisional application No. 60/575,997, filed on Jun. 1, 2004, provisional application No. 60/639,222, filed on Dec. 22, 2004.

(51) Int. Cl.
*C12N 7/00* (2006.01)

(52) U.S. Cl.
CPC ........ *C12N 7/00* (2013.01); *C12N 2750/14151* (2013.01)

(58) Field of Classification Search
None
See application file for complete search history.

(56) References Cited

U.S. PATENT DOCUMENTS

| | | | | |
|---|---|---|---|---|
| 4,138,287 | A * | 2/1979 | Andersson et al. | 435/239 |
| 6,146,874 | A | 11/2000 | Zolotukhin et al. | 435/235.1 |
| 6,194,191 | B1 | 2/2001 | Zhang et al. | 435/235.1 |
| 6,566,118 | B1 | 5/2003 | Atkinson et al. | 435/239 |
| 6,593,123 | B1 | 7/2003 | Wright et al. | 435/239 |
| 2004/0166122 | A1 * | 8/2004 | Evans et al. | 424/204.1 |

FOREIGN PATENT DOCUMENTS

WO  WO99/61643  12/1999

OTHER PUBLICATIONS

Vihinen-Ranta M. et al., Intracellular Route of Canine Parvovirus Entry, Journal of Virology, Jan. 1998, vol. 72, No. 1, pp. 802-806.*
Adadeyoh et al., "Short-Term Field Use and Shipping Stability Study of a Wild Type AD5 Adenoviral Reference Material," BioProcessing, 1(3):62-9 (2002).
Braun et al., "Protein Aggregates Seem to Play a Key Role Among the Parameters Influencing The Antigenicity of Interferon Alpha (IFN-Alpha) in Normal and Transgenic Mice," Pharm. Res. 14(10):1472-1478 (1997).
Chen et al., "Strategies to Suppress Aggregation of Recombinant Keratinocyte Growth Factor During Liquid Formulation Development," J. Pharm. Sci. 83(12):1657-1661 (1994).
Chenuaud et al., "Autoimmune Anemia in Macaques Following Erythropoietin Gene Therapy," Blood 103(9):3303-3304 (2004).
Croyle et al., "Development of Formulations That Enhance Physical Stability of Viral Vectors for Gene Therapy," Gene Therapy 8(17):1281-1290 (2001).
Drittanti et al., "Optimised Helper Virus-Free Production of High Quality Adeno-Associated Virus Vectors", The Journal of Gene Medicine, 3:59-71 (2001).
Flotte, T. R., "Immune Responses to Recombinant Adeno-Associated Virus Vectors: Putting Preclinical Findings Into Perspective," Human Gene Ther. 15(7):716-717 (2004).
Gao et al., "Erythropoietin Gene Therapy Leads to Autoimmune Anemia in Macaques," Blood 103(9):3300-3302 (2004).
High et al., "Human Immune Responses to AAV-2 Capsid May Limit Duration of Expression in Liver-Directed Gene Transfer in Human With Hemophilis β," Blood, 104(11):121a, Abstract No. 413 (2004).
Huang et al., "ADAAV Support High-Titer Production of RAAV But Not Stable," Mol. Therapy 1:S286 (2000).
Meijer et al., "Targeting of Drugs to the Liver," Sem. Liver Dis. 15(3):202-256 (1995).
Qu et al., "Evidence That Ionic Interactions Are Involved in Concentration-Induced Aggregation of Recombinant Adeno-Associated Virus," Molecular Therapy, 7(5):S348, abstract No. 901 (2003).
Qu et al., "Scaling Up Production of Recombinant AAV Vectors for Clinical Applications," Curr Opin Drug Disc Dev. 3(6):750-755 (2000).
Shire et al., "Challenges in The Development of High Protein Concentration Formulations," J. Pharm. Sci. 93(6):1390-1402 (2004).
Sommer et al., "Quantification of Adeno-Associated Virus Particles and Empty Capsids by Optical Density Measurement," Mol Ther 7(1):122-128 (2003).
Steinbach et al., "Assembly of Adeno-Associated Virus Type 2 Capsids in Vitro," J Gen. Virol. 78(6):1453-1462 (1997).
Wang, W., "Instability, Stabilization, and Formulation of Liquid Protein Pharmaceuticals," Int. J. Pharm. 185(2):129-188 (1999).
Won et al., "Stabilizers Against Heat-Induced Aggregation of RPR 114849, An Acidic Fibroblast Growth Factor (AFGF)," Int. J. Pharm. 167:25-36 (1998).
Wright et al., "Recombinant Adeno-Associated Virus: Formulation Challenges and Strategies for a Gene Therapy Vector," Curr. Opin. Drug Disc. Dev. 6(2):174-178 (2003).

(Continued)

*Primary Examiner* — Satyendra Singh

(74) *Attorney, Agent, or Firm* — Roberta L. Robins; Robins Law Group

(57) ABSTRACT

Compositions and methods are provided for preparation of concentrated stock solutions of AAV virions without aggregation. Formulations for AAV preparation and storage are high ionic strength solutions (e.g. μ~500 mM) that are nonetheless isotonic with the intended target tissue. This combination of high ionic strength and modest osmolarity is achieved using salts of high valency, such as sodium citrate. AAV stock solutions up to $6.4 \times 10^{13}$ vg/mL are possible using the formulations of the invention, with no aggregation being observed even after ten freeze-thaw cycles. The surfactant Pluronic® F68 may be added at 0.001% to prevent losses of virions to surfaces during handling. Virion preparations can also be treated with nucleases to eliminate small nucleic acid strands on virions surfaces that exacerbate aggregation.

6 Claims, 3 Drawing Sheets

(56) References Cited

OTHER PUBLICATIONS

Wright et al., "425. Formulation Development for AAV2 Vectors: Identification of Excipients That Inhibit Vector Aggregation," Mol. Ther. [Online] 9(S1):S163-S163 (2004).

Wright et al., "Identification of Factors That Contribute to Recombinant AAV2 Particle Aggregation and Methods to Prevent Its Occurrence During Vector Purification and Formulation," Mol. Ther. 12(1):171-178 (2005).

Xie et al., "Large-Scale Production, Purification and Crystallization of Wild-Type Adeno-Associated Virus-2," J. Virol. Methods 122(1):17-27 (2004).

Xie et al., "The Atomic Structure of Adeno-Associated Virus (AAV-2), A Vector for Human Gene Therapy," Proc. Natl. Acad. Sci. U.S.A. 99(16):10405-10410 (2002).

Zhen et al., "Infectious Titer Assay for Adeno-Associated Virus Vectors With Sufficient to Detect Single Infectious Events," Human Gene Ther. 15:709-715 (2004).

The Term "Purify" and "About", Merriam-Webster Online Dictionary, at the web-http://www.m-w.com, p. 1 and p. 2, Accessed on Nov. 30, 2006, Dec. 1, 2006.

The Definition of the Term "Ionic Strength", Answer.com, at the web-http://www.answers.com, p. 1, Accessed on Nov. 30, 2006.

* cited by examiner

COMPOSITIONS AND METHODS TO PREVENT AAV VECTOR AGGREGATION

CROSS REFERENCE TO RELATED APPLICATIONS

This application is a continuation of U.S. application Ser. No. 11/141,996, now U.S. Pat. No. 7,704,721, from which application priority is claimed pursuant to 35 U.S.C. §120; which application claims the benefit under 35 U.S.C. §119(e) of provisional applications 60/575,997 filed Jun. 1, 2004 and 60/639,222 filed Dec. 22, 2004. The foregoing applications are hereby incorporated by reference in their entireties.

FIELD OF THE INVENTION

The present invention relates to compositions and methods of preparing and storing AAV virions that prevent aggregation.

BACKGROUND

Recombinant adeno-associated virus (rAAV) is a promising vector for human gene transfer. Grimm, D., and Kleinschmidt, J. A. (1999) Hum Gene Ther. 10: 2445-2450; High, K. A. (2001) Ann. N.Y. Acad. Sci. 953: 64-67; Pfeifer, A., and Verma, I. M. (2001) Ann. Rev. Genomics Hum. Genet. 2: 177-211. AAV is a member of the Dependovirus genus of the parvoviruses. AAV serotype 2 (AAV2) is composed of a single-strand DNA molecule of 4680 nucleotides encoding replication (rep) and encapsidation (cap) genes flanked by inverted terminal repeat (ITR) sequences. Berns, K. I. (1996) in Fields Virology (B. N. Fields et. al. Eds.), pp. 2173-2197. Lippincott-Raven Publishers, Philadelphia. The genome is packaged by three capsid proteins (VP1, VP2 and VP3), which are amino-terminal variants of the cap gene product. The resulting icosahedral virus particle has a diameter of ~26 nm. A high resolution crystal structure of AAV2 has been reported. Xie, Q. et al. (2002) Proc. Natl. Acad. Sci. USA. 99: 10405-10410.

The solubility of purified AAV2 virus particles is limited, and aggregation of AAV2 particles has been described as a problem. Croyle, M. A. et al. (2001) Gene Therapy 8: 1281-1290; Huang, J. et al. (2000) Mol. Therapy 1: 5286; Wright, J. F. et al. (2003) Curr. Opin. Drug Disc. Dev. 6: 174-178; Xie, Q. et al. (2004) J. Virol. Methods 122: 17-27. In commonly used buffered-saline solutions, significant aggregation occurs at concentrations of $10^{13}$ particles/mL, and aggregation increases at higher concentrations. Huang and co-workers reported that AAV vectors undergo concentration-dependent aggregation. Huang, J. et al. (2000) Mol. Therapy 1: S286. Xie and coworkers (Xie, Q. et al. (2004) J. Virol. Methods 122: 17-27) similarly reported that at concentrations exceeding 0.1 mg/mL, AAV2 vectors require elevated concentrations of salt to prevent aggregation. Aggregation of AAV2 vectors occurs at particle concentrations exceeding $10^{13}$ particles/mL in commonly used neutral-buffered solutions such as phosphate- and Tris-buffered saline. This corresponds to a protein concentration of ~0.06 mg/mL, and emphasizes the low solubility of AAV2 under these conditions. The effective vector concentration limit may be even lower for vectors purified using column chromatography techniques because excess empty capsids are co-purified and contribute to particle concentration.

Particle aggregation is a significant and not fully resolved issue for adenovirus vectors as well. Stability of a recently established adenovirus reference material (ARM) was recently reported. Adadevoh, K. et al. (2002) BioProcessing 1(2): 62-69. Aggregation of the reference material, formulated in 20 mM Tris, 25 mM NaCl, and 2.5% glycerol at pH 8.0, was assessed by dynamic light scattering, photon correlation spectroscopy and visual appearance. A variable level of vector aggregation following either freeze-thaw cycling or non-frozen storage was observed, resulting in restrictive protocols for the use of the ARM.

Aggregation can lead to losses during purification and inconsistencies in testing of purified vector preparations. The in vivo administration of AAV2 vectors to certain sites, such as the central nervous system, may require small volumes of highly concentrated vector, and the maximum achievable dose may be limited by low vector solubility.

Vector aggregation is also likely to influence biodistribution following in vivo administration, and cause adverse immune responses to vectors following their administration. As has been reported for proteins (Braun, A. et al. (1997) Pharm. Res. 14: 1472-1478), aggregation of vector may increase immunogenicity by targeting the vector to antigen presenting cells, and inducing enhanced immune responses to the capsid proteins and transgene product. The reports of immune responses to AAV vectors in pre-clinical (Chenuaud, P. et al. (2004) Blood 103: 3303-3304; Flotte, T. R. (2004) Human Gene Ther. 15: 716-717; Gao, G. et al. (2004) Blood 103: 3300-3302) and clinical (High, K. A. et al. (2004) Blood 104: 121a) studies illustrate the need to address all factors that may contribute to vector immunogenicity.

Testing protocols to characterize purified vectors are also likely to be affected by vector aggregation. Determination of the infectivity titer of vector was reported to be highly sensitive to vector aggregation. Zhen, Z. et al. (2004) Human Gene Ther. 15: 709-715. An important concern is that vector aggregates may have deleterious consequences following their in vivo administration because their transduction efficiency, biodistribution and immunogenicity may differ from monomeric particles. For example, intravascular delivery of AAV vectors to hepatocytes requires that the vectors pass through the fenestrated endothelial cell lining of hepatic sinusoids. These fenestrations have a radius ranging from 50 to 150 nm (Meijer, K. D. F., and Molema, G. (1995) Sem. Liver Dis. 15: 206) that is predicted to allow the passage of monomeric AAV vectors (diameter ~26 nm), but prevent the passage of larger vector aggregates. In biodistribution studies in mice, aggregated AAV2 vectors labeled with the fluorescent molecule Cy3 were sequestered in liver macrophages following vascular delivery. Huang, J. et al. (2000) Mol. Therapy 1: S286.

Formulation development for virus-based gene transfer vectors is a relatively recent area of investigation, and only a few studies have been reported describing systematic efforts to optimize AAV vector formulation and stability. Croyle, M. A. et al. (2001) Gene Therapy 8: 1281-1290; Wright, J. F. et al. (2003) Curr. Opin. Drug Disc. Dev. 6: 174-178; Xie, Q. et al. (2004) J. Virol. Methods 122: 17-27. Defining formulations compatible with pre-clinical and clinical applications that minimize changes in vector preparations is an important requirement to achieve consistently high vector safety and functional characteristics. As is well established for protein therapeutics (Chen, B. et al. (1994) J. Pharm. Sci. 83: 1657-1661; Shire, S. J. et al. (2004) J. Pharm. Sci. 93: 1390-1402; Wang, W. (1999) Int. J. Pharm. 185: 129-188; Won, C. M. et al. (1998) Int. J. Pharm. 167: 25-36), an important aspect of vector stability is solubility during preparation and storage, and vector aggregation is a problem that needs to be fully addressed. Vector aggregation leads to losses during vector purification, and while aggregates can be removed by filtration, the loss in yield results in higher costs and capacity limitations when producing vector for pre-clinical and clinical studies. Even after filtration to remove aggregates, new aggregates can form in concentrated preparations of AAV2 vector in buffered-saline solutions.

The need exists for improved formulations and methods for purification and storage of AAV vectors, such as rAAV2, that prevent aggregation of virus particles.

SUMMARY OF THE INVENTION

These and other needs in the art are met by the present invention, which provides high ionic strength solutions for use in preparing and storing AAV vectors that maintain high infectivity titer and transduction efficiency, even after freeze-thaw cycles.

In one aspect the invention relates to methods of preventing aggregation of virions in a preparation of virions by adding excipients to achieve an ionic strength high enough to prevent aggregation. In another aspect the invention relates to compositions of virions having an ionic strength high enough to prevent aggregation.

In some embodiments of the invention, the ionic strength is at least about 150 mM, 200 mM, 250 mM, 300 mM, 350 mM, 400 mM, 450 mM, 500 mM, 600 mM, 700 mM or more. In some embodiments this ionic strength is accomplished using excipients comprising one or more multivalent ions, for example citrate, sulfate, magnesium or phosphate.

In additional embodiments, the osmolarity of the preparation of virions is maintained at near isotonic levels, for example 200 mOsm, 250 mOsm, 280 mOsm, 300 mOsm, 350 mOsm or 400 mOsm, even though the ionic strength is high enough to prevent virion aggregation.

In some embodiments the virions are adeno-associated virus (AAV) virions, for example AAV-2.

In other embodiments of the methods of the present invention preparations of virions are treated with a nuclease, for example Benzonase®. In further embodiments, nuclease treatment is combined with addition of excipients that achieve an ionic strength high enough to prevent aggregation.

In some embodiments of the present invention, the surfactant Pluronic® F68 is added to a preparation of virions, for example to 0.001%. In one embodiment, the composition comprises purified virus particles, 10 mM Tris pH 8.0, 100 mM sodium citrate and 0.001% Pluronic® F68.

In one embodiment, AAV vectors can be stored as compositions of the present invention at concentrations exceeding $1\times10^{13}$ vg/mL, for example $2\times10^{13}$, $3\times10^{13}$, $4\times10^{13}$, $5\times10^{13}$ and up to $6.4\times10^{13}$ vg/mL, without significant aggregation. In some embodiments, AAV vectors stored using the methods and compositions of the invention do not exhibit significant aggregation when stored at 4° C. for five days. In other embodiments, AAV vectors that are stored as such compositions do not exhibit significant aggregation after one, five, ten or more freeze-thaw cycles at −20° C. or at −80° C.

In some embodiments, preparations of virions stored according to the methods and compositions of the invention exhibit an average particle radius (Rh), as measured by dynamic light scattering, indicating that no significant aggregation of virions has taken place. In some embodiments, preparations of virions stored according to the methods and compositions of the invention exhibit an average particle radius (Rh) greater than about 15 nm, 20 nm, or 30 nm.

In some embodiments, recovery of virions from preparations of virions stored according to the methods and compositions of the invention is greater than about 85%, 90% or 95% following filtration through a 0.22 μm filter.

In yet another aspect, the invention relates to kits comprising the high ionic strength formulations of the invention. In one embodiment the kit comprises a pre-mixed solution of excipients. In another embodiment the kit comprises two or more separate components of a high ionic strength composition of the present invention to be mixed by a user. In some embodiments the kit comprises sodium citrate, Tris® and Pluronic® F68. In other embodiments, the kit further comprises instructions for making a composition or performing a method of the present invention.

DETAILED DESCRIPTION OF THE INVENTION

Figure 1:
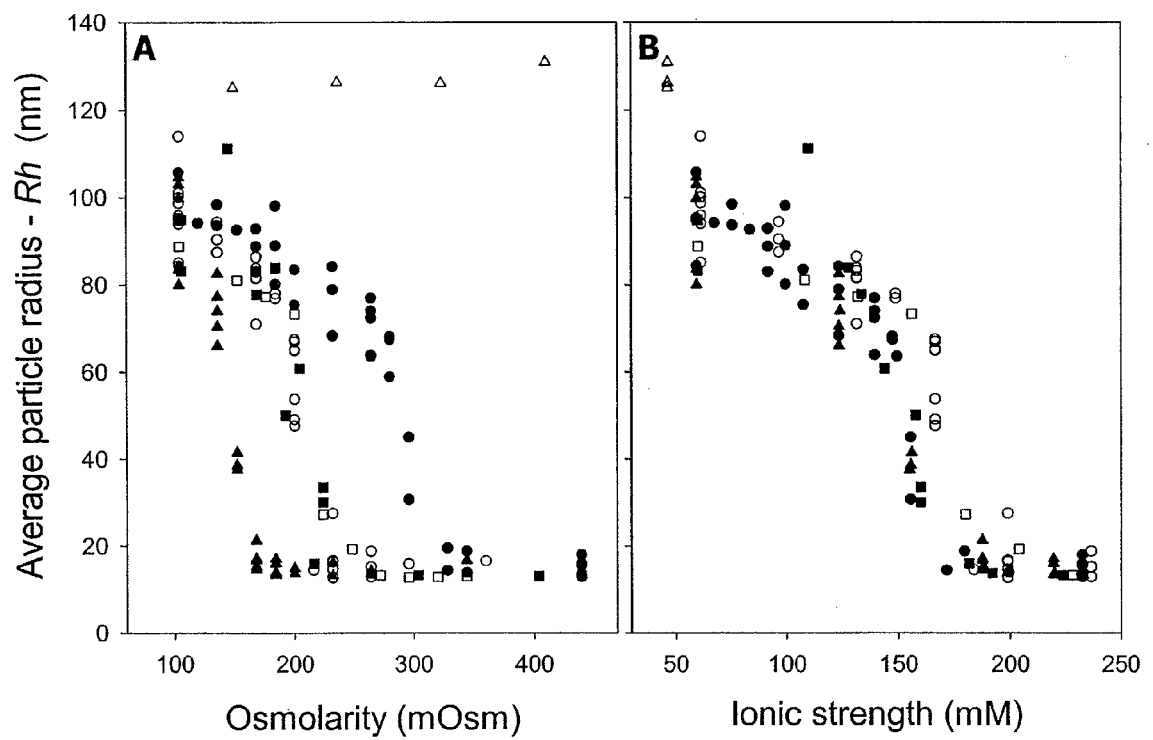
FIGS. 1A and 1B present data showing aggregation of AAV2-FIX particles as a function of osmolarity (FIG. 1A) or ionic strength (FIG. 1B) for various buffer compositions. AAV2-FIX vectors are prepared by Method 2 of Example 1. Average particle radius is measured by dynamic light scattering (DLS) following vector dilution in varying concentrations of excipients buffered with 10 mM sodium phosphate at pH 7.5. Excipients include sodium chloride (●), sodium citrate (○), sodium phosphate (■), sodium sulfate (□), magnesium sulfate (▲), and glycerol (Δ).

AAV2 vector aggregation is frequently observed in concentrated preparations of vectors and can affect purification recovery, and in vivo potency and safety. Hence, an important objective for the development AAV2 vectors is to identify methods and formulations that prevent aggregation of vectors when concentrated stocks are prepared.

Unless otherwise indicated, the term "vector" as used herein refers to a recombinant AAV virion, or virus particle, regardless of the frequent use of "vector" to also refer to non-viral DNA molecules, such as plasmids, in other contexts.

The present invention is based in part on the observation that solution ionic strength is an important parameter in AAV vector aggregation, implicating the involvement of ionic interactions between virus particles in the aggregation process. The observation that elevated ionic strength increases AAV2 vector solubility regardless of the identity of the charged excipient supports the hypothesis that ionic strength of solution per se, rather than interactions involving a specific ionic species, is the relevant physico-chemical parameter. A threshold ionic strength of at least 200 mM is required to prevent aggregation at vector particle concentrations examined herein.

Of practical concern, commonly used buffered saline solutions have insufficient ionic strength to prevent AAV2 vector aggregation at concentrations exceeding $10^{13}$ particles/mL. It is known that high salt concentrations increase AAV2 vector solubility (e.g. highly concentrated AAV2 vectors recovered from gradients generally remain soluble in concentrated CsCl). However, optimal formulations for pre-clinical and clinical studies should be close to isotonic (280-400 mOsm), especially for in vivo administration of vector to sites where dilution of hypertonic solutions may be slow. In embodiments of the present invention the exponential relationship of ionic strength with charge valency is used to develop isotonic formulations with high ionic strengths. Salt species with multiple charge valencies (e.g. salts of sulfate, citrate, and phosphate) that are commonly used as excipients in human parenteral formulations can provide the level of ionic strength needed to prevent AAV2 vector aggregation when used at isotonic concentrations. While isotonic (150 mM) sodium chloride has an ionic strength of 150 mM, a value insufficient to maintain AAV2 solubility at high vector concentrations, isotonic sodium citrate, with an ionic strength of ~500 mM, can support AAV2 vector concentrations of at least $6.4 \times 10^{13}$ vg/mL without aggregation.

Without intending to be limited by theory, the low solubility of AAV2 particles may be caused by their highly symmetrical nature in conjunction with the stabilizing effect of complementary charged regions between neighbouring particles in aggregates. The surface charge density based on the crystal structure of AAV2 (Xie, Q. et al. (2002) *Proc. Natl. Acad. Sci. U.S.A.* 99: 10405-10410) reveals a pattern of positive and negative charges on the virus surface. Previous reports have shown that AAV2 vector aggregation is pH dependent, and hypothesized that amino acids with charged side groups are involved in inter-particle binding. Qu, G. et al. (2003) *Mol. Therapy* 7: S238. These reports hypothesized that if charged amino acid side chains are involved in vector aggregation, high concentrations of free amino acids could block vector particle interactions. However, we have found that amino acids with charged side chains are not effective in preventing AAV2 vector aggregation beyond their contribution to ionic strength.

Vector aggregation at low ionic strength was also found to be reduced but not prevented by efficient nuclease treatment of purified vector particles. Digestion at an earlier stage of the purification process (clarified HEK cell lysate) did not reduce aggregation following vector purification. It is likely that digestion of already purified virions is more efficient because of a higher enzyme to nucleic acid substrate ratio. One mechanism to explain these results is that residual nucleic acid impurities (e.g. host cell and plasmid DNA) bound to the vector surface can bridge to binding sites on neighbouring virus particles and thus cause aggregation. Purified AAV2 vectors (empty capsid free) have been reported to contain approximately 1% non-vector DNA. Smith, P. et al. (2003) *Mol. Therapy* 7: 5348. While >50% of this non-vector DNA was reported to be nuclease resistant and was packaged within capsid particles, some impurity DNA was nuclease resistant and appeared to be associated with the surface of purified vector particles. The observation that efficient nuclease treatment can reduce vector aggregation suggests that nucleic acids associated with the vector surface at an average level not greater than ~25 nucleotides per vector particle can contribute to AAV vector aggregation.

In summary, the use of high ionic strength solutions during AAV2 vector purification and final formulation, and efficient removal of residual vector surface DNA are two effective strategies to achieve highly concentrated solutions of AAV2 vectors for use in pre-clinical and clinical studies. High ionic strength solutions and nuclease treatment can be used in combination or separately. Although data were obtained using AAV2 vectors, the composition and methods of the present invention may also be useful with other AAV serotypes/variants, or other viral vectors such as adenoviruses, lentiviruses and retroviruses.

AAV Aggregation as a Function of Excipient Concentration

Initial screening experiments are performed to elucidate the mechanism of AAV vector aggregation and to identify classes of excipients that can reduce/prevent aggregation. Vector aggregation can be caused by dilution (5-fold) of vector in neutral-buffered saline with low concentration buffer (20 mM sodium phosphate, pH 7.2). Excipients are screened using this "dilution-stress" method to identify excipients that are able to prevent vector aggregation when included in the diluent. For screening, aggregation is measured by dynamic light scattering (DLS). Classes of excipients examined included selected inorganic salts, amino acids, uncharged carbohydrates, and surfactants. Results are presented in Table 1.

TABLE 1

SCREENING FOR EXCIPIENTS THAT PREVENT AAV2 VECTOR AGGREGATION USING DILUTION-STRESS METHOD

| Excipient | Osm required to prevent aggregation (max tested) |
|---|---|
| Magnesium sulfate | 180 mOsm |
| Sodium citrate | 220 mOsm |
| Sodium chloride | 320 mOsm |
| Sodium phosphate | 220 mOsm |
| Sodium sulfate | 220 mOsm |
| Arginine | NIA (200 mOsm) |
| Aspartic acid | 320 mOsm |
| Glutamic acid | 320 mOsm |
| Glycine | NIA (200 mOsm) |
| Histidine | NIA (200 mOsm) |
| Lysine | 300 mOsm |
| Glycerol | NIA (5% w/v, 543 mOsm) |
| Iodixanol | NIA (5% w/v, 32 mOsm) |
| Mannitol | NIA (5% w/v, 275 mOsm) |
| Sorbitol | NIA (5% w/v, 275 mOsm) |
| Sucrose | NIA (5% w/v, 146 mOsm) |
| Trehalose | NIA (5% w/v, 146 mOsm) |
| Pluronic ® F68 | NIA (10% w/v, 12 mOsm) |
| Polysorbate 80 | NIA (1% w/v) |

NIA: No inhibition of aggregation

As illustrated in Table 1, charged excipients (inorganic salts and amino acids) prevent aggregation when present at sufficient concentrations. However, salt concentrations required to prevent vector aggregation vary, ranging from 180 mOsm for magnesium sulfate, to 320 mOsm for sodium chloride. The amino acids arginine, aspartic acid, glutamic acid, glycine, histidine, and lysine do not prevent aggregation at 200 mOsm, but lysine, aspartic acid, and glutamic acid prevent aggregation at 300-320 mOsm. Arginine, glycine and histidine were not tested at concentrations other than 200 mOsm. Selected carbohydrates have no effect on vector particle aggregation when present at concentrations up to 5% w/v. For example, 5% w/v glycerol (543 mOsm) does not prevent aggregation. The surfactants Polysorbate80 (1% w/v) and Pluronic® F68 (10% w/v) similarly have no effect on aggregation using the "dilution-stress" method.

AAV Aggregation as a Function of Osmolarity and Ionic Strength

FIGS. 1A and 1B show the results of a more detailed analysis of vector aggregation as a function of the concentration of various salts. FIG. 1A shows vector aggregation as a function of the osmolarity of selected excipients. For charged species a concentration-dependent inhibition of AAV2 vector aggregation is observed. Salts with multivalent ions achieve a similar degree of inhibition of aggregation at lower concentrations than monovalent sodium chloride. For example, magnesium sulfate prevents aggregation at >200 mOsm whereas sodium chloride requires ≥350 mOsm to achieve a similar effect. Sodium citrate, sodium sulfate, and sodium phosphate are intermediate in their potency to prevent vector aggregation.

Although the results in FIG. 1A and Table 1 show no effect of glycerol and certain sugars at concentrations up to 5% on AAV2 vector aggregation induced by low ionic strength, the data cannot rule out improvement of AAV2 solubility at glycerol concentrations above 5%. For example, Xie and co-workers reported that 25% (w/v) glycerol enabled concentration of AAV2 to very high concentrations (4.4 to $18 \times 10^{14}$ particles/ml) in low ionic strength solutions. Xie, Q. et al. (2004) *J. Virol. Methods* 122: 17-27.

FIG. 1B shows the data of FIG. 1A plotted as a function of the calculated ionic strength, rather than osmolarity, for each excipient. FIG. 1B demonstrates that vector aggregation is prevented when ionic strength is ~200 mM or greater regardless of which salt is used. These data suggested that the ionic strength ($\mu$) of a solution, a parameter that depends on both solute concentration and charge valency, is the primary factor affecting aggregation.

Ionic strengths useful to prevent aggregation in embodiments of the present invention include, for example, 250 mM, 300 mM, 350 mM, 400 mM, 450 mM, 500 mM, 600 mM, 700 mM or higher ionic strengths. Multivalent ions are preferred to achieve these ionic strengths in methods and formulations of the present invention, such as divalent, trivalent, tetravalent, pentavalent ions and ions of even higher valency. The pH buffer in solutions and formulations of the present invention may be phosphate, Tris, or HEPES (or other Good's buffers), but any other suitable pH buffer may be used. In preferred embodiments, the multivalent ions and buffer are selected to be compatible with the target tissue for the vector being prepared.

Use of multivalent ions in the methods and compositions of the invention makes it possible to create compositions of high ionic strength but relatively low osmolarity. High ionic strength compositions of the present invention may be nearly isotonic, and may be, for example, about 200 mOsm, 250 mOsm, 280 mOsm, 300 mOsm, 350 mOsm or 400 mOsm, although other osmolarities may be acceptable for some uses of the compositions.

AAV Aggregation as a Function of the Method of AAV Purification

Figure 2:
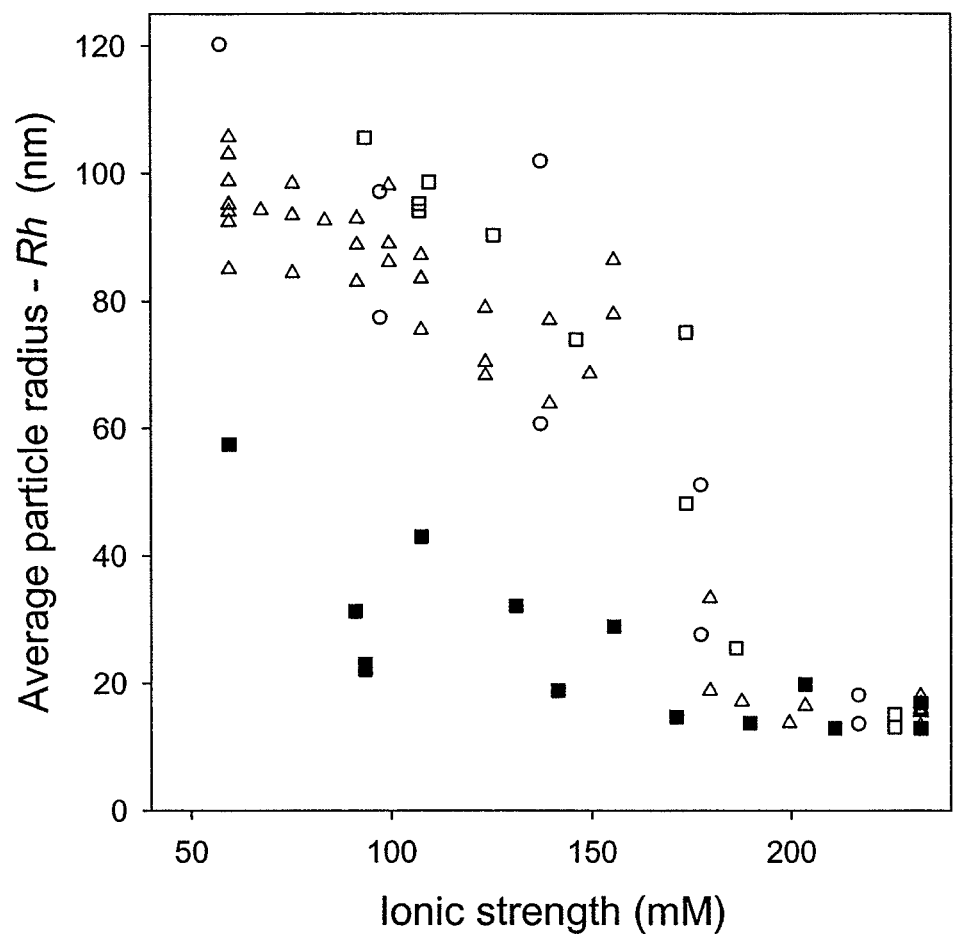
FIG. 2 presents data on AAV2-FIX aggregation as a function of the method of purification. The average particle radius is measured by DLS following vector dilution in varying concentrations of sodium chloride buffered with 10 mM sodium phosphate at pH 7.5. Vectors are purified by Method 1 (double CsCl gradient) (○); Method 2 (cation exchange chromatography) (□); Method 2 plus nuclease digestion (■); or Method 3 (chromatography plus one CsCl gradient) (Δ). Purification Methods 1-3 are described in Example 1.

Recombinant AAV2 purified using different methods (e.g. density gradient purification versus ion-exchange chromatography) would be expected to have different impurity profiles. FIG. 2 shows vector aggregation as a function of ionic strength for several preparations of AAV differing in the purification method. Purification methods are described in Example 1. Sodium chloride is used to vary the ionic strength. AAV2-FIX vectors purified by double cesium chloride gradient ultracentrifugation (Method 1), by cation exchange column chromatography (Method 2), or by combined column and cesium chloride gradient ultracentrifugation (Method 3) each demonstrate similar aggregation responses as ionic strength is decreased. In contrast, AAV2-FIX purified by the column method and then subjected to a nuclease digestion step (Method 2+nuclease) shows reduced aggregation at low ionic strength.

AAV Aggregation at Preparative Scale

The data in Table 1 and FIGS. 1A, 1B and 2 involve vector aggregation at an analytical scale, employing DLS to measure aggregation. Table 2, in contrast, shows the effects of elevated ionic strength and nuclease treatment on AAV2 vector aggregation at a larger scale, using methods to induce and quantify vector aggregation that are relevant to preparative scale vector purification. Experimental details are provided in Example 2. Purified AAV vectors are diafiltered into solutions of various ionic strengths, the volume is reduced to achieve high vector concentrations, and aggregation is then assessed by measuring vector recovery after filtration through a 0.22 μm filter. Aliquots from a single pool of AAV2-AADC vector purified by Method 1 through the second CsCl gradient centrifugation step ($1.8 \times 10^{15}$ vg in 91 mL, $1.8 \times 10^{13}$ vg/mL, in ~3M CsCl) are used as starting material in the diafiltration experiments. Tangential flow filtration using hollow fibers is used for diafiltration because it is scalable and yet it still enables preparation of volumes (min. 1.4 mL), and thus AAV concentrations, at which aggregation would be expected in neutral buffered saline.

In Experiment 1, three hollow fiber units are used to diafilter AAV2-AADC vector in formulations CF, TF1, or TF2, and the volume is reduced to a target of $2.5 \times 10^{13}$ vg/mL. See Example 2. The samples are then filtered through a 0.22 μm filter. Results are shown in Table 2. Vector recovery ("Yield %") for both elevated ionic strength formulations TF1 (95±7.4%) and TF2 (93±7.4%) are significantly higher than the recovery using the control formulation CF (77±6.6%).

TABLE 2

AAV VECTOR RECOVERY AT PROCESS SCALE

| Experiment | Formulation | μ (mM) | Target (vg/mL) | Actual (vg/mL) | Yield % (RSD) |
|---|---|---|---|---|---|
| 1 | CF | 160 | 2.5E13 | 1.93E13 | 77 (6.6) |
| 1 | TF1 | 310 | 2.5E13 | 2.38E13 | 95 (7.4) |
| 1 | TF2 | 510 | 2.5E13 | 2.33E13 | 93 (7.4) |
| 2 | CF | 160 | 6.7E13 | 3.98E13 | 59 (6.0) |
| 2 | TF2 | 510 | 6.7E13 | 6.42E13 | 96 (4.4) |
| 3 | CF (−Bz) | 160 | 3.6E13 | 2.46E13 | 68 (11) |
| 3 | CF (+Bz) | 160 | 3.6E13 | 3.29E13 | 91 (12) |

In Experiment 2, AAV2-AADC is concentrated to a higher target value ($6.7 \times 10^1$ vg/mL) in CF or TF2. Vector recovery using TF2 (96±4.4%) is again significantly higher than recovery using CF (59±6.0%). Within the variability of the assays used, vector was recovered fully at both target concentrations using TF2, indicating that aggregation was prevented. In contrast, significant aggregation was observed at both target concentrations using CF, and the extent of aggregation (i.e. loss following 0.22 μm filtration) was higher at the higher target vector concentration. In an additional experiment (not shown), 50 μL samples of AAV2 vector are taken following concentration but prior to the 0.22 μm filtration step of Experiment 2, and examined by light microscopy. Vector concentrated in CF contains obvious amounts of visible material (not shown), while no such material is seen in vector concentrated in TF2.

Experiment 3 examines the effect of prior nuclease digestion of purified vector on aggregation. In the absence of nuclease digestion recovery of AAV2-AADC in CF is 68±11%, similar to the recoveries in Experiments 1 and 2. In contrast, purified vector treated with nuclease and then concentrated in CF gives higher recovery (91±12%). These prep scale results reflect the same effect of nuclease digestion shown in FIG. 2 using the "dilution-stress" (analytical scale) method.

The results presented in Table 2 demonstrate that the methods and compositions of the present invention increase the recovery of AAV vector recovery. For example, in various embodiments of the present invention, recovery is improved from less than about 80% to at least about 85%, 90%, 95% or more.

AAV Stability and Activity Following Storage or Freeze-Thaw Cycling

Croyle and coworkers reported a significant loss of titer of AAV and adenovirus following multiple freeze-thaw cycling in sodium phosphate buffer, and demonstrated that the better pH buffering provided by potassium phosphate during freeze-thaw cycling prevented titer loss. Croyle, M. A. et al. (2001) *Gene Therapy* 8: 1281-1290. Results of our freeze-thaw stability study using sodium phosphate support these findings. We find that while 150 mM sodium phosphate provides sufficient ionic strength to prevent aggregation during preparation and non-frozen storage of concentrated AAV2-AADC vector, even a single freeze-thaw cycle at −20 or −80° C. results in aggregation.

AAV stability after storage or freeze-thaw (F/T) cycling is assessed in buffers of the present invention as follows. The concentrated vectors prepared in CF, TF1, and TF2 (Table 2, Experiment 1) are subjected to a short stability study to investigate whether aggregation will occur during refrigerated storage, or following multiple freeze-thaw (F/T) cycles. Aggregation is assessed by DLS using undiluted samples, and Rh values >20 nm are deemed to indicate the occurrence of some level of aggregation.

TABLE 3

STABILITY OF AAV2 VECTORS

| Formu-lation | Particle radius - Rh (nm) | | | | | | | |
|---|---|---|---|---|---|---|---|---|
| | 4° C. | −20° C. | | | −80° C. | | | |
| | Pre | 5 d | 1 F/T | 5 F/T | 10 F/T | 1 F/T | 5 F/T | 10 F/T |
| CF | 14.5 | 27.0 | 22.4 | 56.1 | 94.5 | 20.6 | 57.5 | 141 |
| TF1 | 13.8 | 16.3 | TH | TH | TH | TH | TH | TH |
| TF2 | 13.8 | 14.4 | 14.2 | 14.0 | 14.1 | 13.8 | 21.3 | 50.9 |

Pre: DLS radius measured immediately following 0.2 μm filtration.
Vector concentrations (vg/mL): CF: 1.93E13, TF1: 2.38E13, TF2: 2.33E13.
TH: signal intensity is too high to measure because of extensive aggregation.

As shown in Table 3, AAV2-AADC vector prepared in CF shows some aggregation after 5 days of storage at 4° C., as well as following one or more F/T cycles at −20 or −80° C. For vector prepared in TF1, no aggregation occurs after 5 days at 4° C., but aggregation occurs following a single F/T cycle at −20 or −80° C. as indicated by a DLS signal intensity that is too high to measure. Visual inspection of these samples reveals slight cloudiness, which is consistent with aggregation. For vector prepared in TF2, no aggregation is observed at 4° C., or following up to 10 F/T cycles at −20° C. Some aggregation is observed following 5 and 10 F/T cycles at −80° C.

AAV activity after storage or F/T cycling in TF2 is assessed as follows. As described above, the high ionic strength, isotonic formulation TF2 effectively prevents vector aggregation during concentration and storage, and therefore represents a promising candidate for further study. An important question is whether preparation and storage of the vector in high ionic strength TF2 would adversely affect its functional activity. To assess this, assays are performed to measure the infectious titer and the transduction efficiency of vectors prepared and stored for an extended period of time in TF2.

For infectivity, a highly sensitive infectivity assay capable of detecting single infectious events is used. Zhen, Z. et al. (2004) *Human Gene Ther.* 15: 709-715. AAV2-AADC is prepared in TF2 at a concentration of $6.4 \times 10^{13}$ vg/mL. After being stored for 45 days at 4° C. the preparation has a vector genome to infectious unit ratio (vg/IU) of 13, compared to a value of 16 vg/IU for the reference vector. This difference is not significant given the reported variability of this assay (RSD ~50%).

Figure 3:
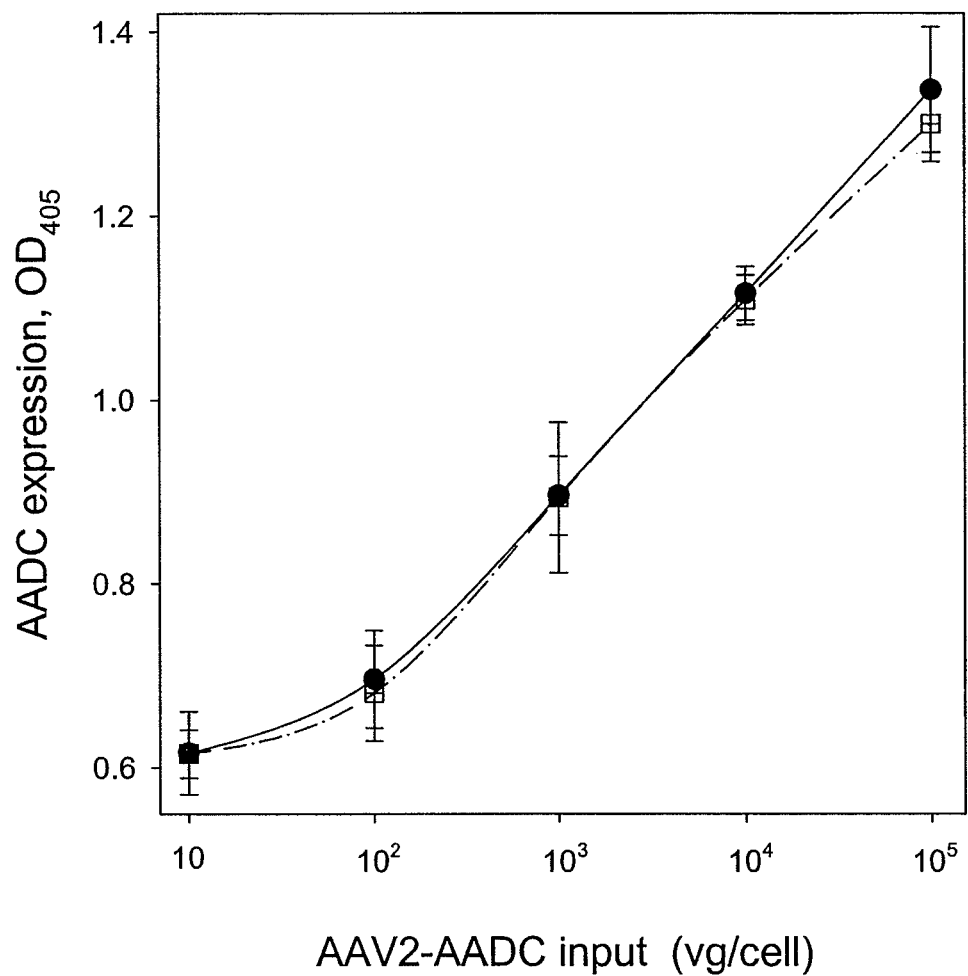
FIG. 3 presents data on transgene expression from D7/4 cells transduced with rAAV2-AADC virions prepared and stored in high ionic strength formulation (□) or in a control formulation (●). The concentration of AADC was measured by ELISA (in triplicate for each data point) 72 hours post-transduction. Error bars represent standard deviations.

Transduction efficiency is assessed by measuring the expression of AADC protein by ELISA following transduction of D7/4 cells. FIG. 3 shows no significant difference between vector prepared in TF2 and the reference control for vector input ranging from 10 to $10^5$ vg/cell. Together, these data indicate that preparation and storage of AAV2 vectors in high ionic strength TF2 does not have a deleterious effect on vector infectivity or transduction efficiency.

CONCLUSION

The effect of ionic strength (μ) on virus particle interactions is determined to elucidate the mechanism of vector aggregation. The ionic strength of neutral-buffered isotonic saline (μ=150 mM) is insufficient to prevent aggregation of AAV2 vectors purified by gradient ultracentrifugation or by cation exchange chromatography at concentrations exceeding $\sim 10^{13}$ particles/mL. Inclusion of sugars (sorbitol, sucrose, mannitol, trehalose, glycerol) at concentrations up to 5% (w/v) or of surfactants Tween80® (1%) or Pluronic® F68 (10%) does not prevent aggregation of vector particles.

In contrast, vector particles remain soluble when elevated ionic strength solutions (μ>200 mM) are used during purification and for final vector formulation. Elevated ionic strength solutions using isotonic excipient concentrations for in vivo administration are prepared with salts of multivalent ions, including sodium citrate, sodium phosphate, and magnesium sulfate. An isotonic formulation containing 10 mM Tris, 100 mM sodium citrate, 0.001% Pluronic® F68, pH 8.0 (μ~500 mM) enables concentration of AAV2-AADC vectors to $6.4 \times 10^{13}$ vg/mL with no aggregation observed during preparation and following ten freeze-thaw cycles at −20° C. See Table 3, below, and accompanying discussion. AAV2-AADC vectors prepared and stored for an extended period in elevated ionic strength formulation retain high infectivity titer (13 IU/vg) and transduction efficiency.

Nuclease treatment of purified AAV2 vectors reduces the degree of vector aggregation, implicating vector surface nucleic acid impurities in inter-particle interactions. Hence, purification methods to efficiently remove vector surface residual nucleic acids, coupled with the use of elevated ionic strength isotonic formulations, are useful methods to prevent AAV2 vector aggregation.

Example 1

AAV Purification Methods

AAV2 vectors expressing human coagulation factor IX (FIX) or human amino acid decarboxylase (AADC) are produced by triple transfection of HEK293 cells as previously described (Matsushita, T. et al. (1998) *Gene Therapy* 5: 938-945), with modifications. For the large scale preparations, cells are cultured and transfected in 850 mm² roller bottles (Corning). Vectors are purified by one of three methods.

In purification Method 1, modified from Matsushita, transfected HEK293 cells in roller bottles are collected by centrifugation (1000 g, 15 min), resuspended in 10 mM sodium phosphate, 500 mM sodium chloride, pH 7.2, and lysed by three freeze/thaw cycles (alternating an ethanol/dry ice bath and a 37° C. water bath). The cell lysate is clarified by centrifugation (8,000 g, 15 min). The supernatant is then diluted to 200 mM NaCl by addition of 10 mM sodium phosphate, pH 7.2, and digested with Benzonase® (Merck, Purity Grade 1; 200 U/mL, 1 h, 37° C.). The lysate is adjusted to 25 mM $CaCl_2$ using a 1M stock solution, and incubated at 4° C. for one hour.

The mixture is centrifuged (8,000 g, 15 min), and the supernatant containing vector is collected. To precipitate virus from the clarified cell lysate, polyethylene glycol (PEG8000) is added to a final concentration of 8%, the mixture incubated at 4° C. for three hours, and then centrifuged (8,000 g, 15 min). The pellets containing vector are re-suspended with mixing in 0.15M NaCl, 50 mM Hepes, 25 mM EDTA, pH 8.0 and incubated at 4° C. for 16 hours. The resuspended material is pooled, and solid cesium chloride is added to a final density of 1.40 gm/ml. Vector is then banded by ultracentrifugation (SW28, 27,000 rpm, 24 h, 20° C.) using a Beckman model LE-80 centrifuge. The centrifugation tubes are fractionated, and densities from 1.38 to 1.42 gm/mL containing vector are pooled. This material is banded a second time by ultracentrifugation (NVT65 rotor, 65,000 rpm, 16 h, 20° C.), and fractions containing purified AAV2 vectors are pooled. To concentrate vector and to perform buffer exchange, vectors in concentrated cesium chloride solution are subjected to ultrafiltration/diafiltration (UF/DF) by tangential flow filtration as described below (Example 2).

In purification Method 2, cell harvests containing AAV are microfluidized and filtered sequentially through 0.65 and 0.22 μm filters (Sartorius). Virus is purified from the clarified cell lysates by cation exchange chromatography using Poros HS50 resin as previously described. U.S. Pat. No. 6,593,123. For the nuclease digestion described in FIG. 2, column-purified vectors are incubated (4 h, RT) with 100 U/mL Benzonase and 10 U/mL DNAse I (RNAse free, Roche Diagnostics, Indianapolis, Ind.).

For purification Method 3, AAV2 vectors purified by cation exchange chromatography are subjected to an additional cesium chloride gradient ultracentrifugation step (SW28, 27,000 rpm, 20 h) to remove empty capsids prior to UF/DF.

Real time quantitative PCR (Q-PCR) is used to quantify AAV preparations as previously described. Sommer, J. M. et al. (2003) *Mol. Therapy* 7: 122-128. Vectors purified by each of the three methods are analyzed by SDS-PAGE/silver staining analysis, and in all cases VP1, VP2 and VP3 are present in the expected ratios, with the capsid proteins representing >95% of total proteins as determined by scanning densitometry. However, unlike gradient-purified AAV2 vectors purified using Methods 1 and 3, vectors purified by Method 2 (column chromatography) contain empty capsids, ranging from 3-10 empty capsids per vector genome.

Example 2

Ultrafiltration and Diafiltration to Detect AAV Aggregation

Disposable hollow fiber tangential flow filtration devices (Amersham BioSciences 8" Midgee, 100 kDa nominal pore size) are used to concentrate and diafilter AAV2 vectors purified by the methods described above, and for the UF/DF experiments described in Table 2. For all UF/DF procedures a volume of diafiltration buffer corresponding to 10× the product volume is used, and it is added in ~1 mL increments to approximate continuous diafiltration. Using this method, the calculated residual CsCl after diafiltration is <0.5 mM.

The following three formulations were used for UF/DF: Control Formulation (CF: 140 mM sodium chloride, 10 mM sodium phosphate, 5% sorbitol, pH 7.3); Test Formulation 1 (TF1: 150 mM sodium phosphate, pH7.5); and Test Formulation 2 (TF2: 100 mM sodium citrate, 10 mM Tris, pH8.0). For Experiment 1 shown in Table 2, diafiltration is performed at a volume corresponding to a vector concentration of $1\times10^{13}$ vg/mL, and following diafiltration the volume is reduced to a value corresponding to $2.5\times10^{13}$ vg/mL (assuming no vector loss).

For Experiment 2, diafiltration is performed at a volume corresponding to a $2\times10^{13}$ vg/mL, and the volume is then reduced to a value corresponding to $6.7\times10^{13}$ vg/mL.

For Experiment 3 (CF±Bz), AAV2-AADC (approximately $1.2\times10^{14}$ vg) is first diafiltered into TF1 (a formulation compatible with nuclease activity) and then passed through a 0.22 μm filter. The titer of this material is determined, and the volume is adjusted to correspond to a concentration of $1\times10^{13}$ vg/mL. To 10 mL of this material, $MgCl_2$ is added to a concentration of 2 mM, and then divided into two equal aliquots. One aliquot is incubated with Benzonase (200 U/mL, 4 h, RT), and the second is mock-incubated. Each aliquot is then diafiltered at a volume corresponding to a vector concentration $2\times10^{13}$ vg/mL, and then concentrated to a $3.6\times10^{13}$ vg/mL target. Following all UF/DF protocols, Pluronic® F-68 (BASF Corp., Mount Olive, N.J.) from a 1% stock is added to the vector product to a final concentration of 0.001%, and the solution is passed through a 0.22 μm syringe filter (Sartorius). All UF/DF procedures are performed in a laminar flow cabinet.

Example 3

Measurement of Vector Aggregation by Dynamic Light Scattering

Purified vectors are analyzed for aggregation by dynamic light scattering (DLS) using a Protein Solutions DynaPro 99 (λ=825.4 nm). Primary data (particle radius—Rh, average value measured over 30 cycles, 10 cycles/min) are used for all analyses reported. A "dilution-stress" method is used to assess the effect of varying excipients on vector aggregation. In this method, 80 μL of test diluent is added to 20 μL of vector solution with mixing in the actual cuvette used for DLS measurement, and data collection is initiated within 10 seconds of mixing. Prior to addition of test diluents, the Rh value for AAV2 vector preparations is measured and confirmed to be <15 nm to ensure that the starting material is monomeric. Samples that are not 100% monomeric are passed through a 0.22 μm syringe disc filter (Sartorius, low protein binding) to remove aggregates.

The osmolarity and ionic strength values given in FIGS. 1 and 2 are calculated using all excipients present in the mixture (i.e. weighted: test diluent (80%) and starting vector formulation (20%)). Osmolarity is calculated according to the equation: Osmolarity=$\Sigma c_i$, where $c_i$ is the molar concentration of each solute species. The ionic strength (μ) is calculated according to the equation: $\mu=\frac{1}{2}\Sigma c_i z_i^2$, where $z_i$ is the charge on each species. In conditions that resulted in vector aggregation (e.g. low μ) a progressive increase in Rh is observed over the course of data collection. To validate the use of the average Rh measured over the 3 minute interval following dilution as a reliable measure of aggregation, the average rate of increase of Rh (ΔRh/Δt) over the same time interval is also determined (not shown). Analysis of ΔRh/Δt gives results concordant with those obtained using the average Rh value reported in FIGS. 1 and 2.

Example 4

AAV Virion Infectivity

Infectivity of AAV2-AADC vectors is determined using a highly sensitive assay as previously described. Zhen, Z. et al. (2004) *Human Gene Ther.* 15: 709-715. Briefly, samples are serially diluted (10-fold dilutions, 10 replicates/dilution) and added to D7/4 cells (modified HeLa cells expressing AAV rep and cap) grown in 96 well tissue culture plates (Falcon, cat. #353227) in DMEM medium containing 10% FBS. Adenovirus (Ad-5, 100 vp/cell) is added to each well to provide helper functions. After 48 h, replication of AAV vector in each well is quantified by Q-PCR using transgene-specific primers and probes, and the frequency of infection at limiting dilution is analyzed by the Karber method to calculate the infectivity titer. The test sample is run concurrently with an AAV2-AADC reference previously prepared in CF and stored at −80° C.

The transduction efficiency of AAV2 vectors is quantified by a whole cell ELISA. D7/4 cells grown in 96 well plates are infected with 10-fold serial dilutions of the test sample and reference vector, corresponding to 10 to $10^5$ vg/cell input (5 replicates/dilution). After 48 h, the culture medium is removed, and cells are washed twice with 200 μL PBS (10 mM sodium phosphate, 140 mM sodium chloride, pH 7.2). Cells are then permeabilized and fixed by addition of 100 μL of PBS containing 0.5% Triton X-100 and 4% paraformaldehyde to each well (15 min). The fixing solution is removed, and the cells are washed twice with PBS containing 0.5% Triton X-100. Non-specific sites are blocked by adding PBS containing 3% bovine serum albumin (BSA) and 0.5% Triton X-100 (60 min).

After washing, cells are incubated for one hour with rabbit anti-AADC IgG antibody (Chemicon, AB136), and washed. Cells are then incubated for one hour with alkaline phosphatase-conjugated goat anti-rabbit IgG, and washed. Antibodies are diluted 1:1000 in PBS containing 1% BSA, 0.5% Triton X-100. Substrate (PNPP, Pierce, cat. #34047) is then added (1 mg/mL in 1× diethanolamine substrate buffer, Pierce, cat. #34064), and after incubation for 30 min the concentration of cleaved substrate is measured spectrophotometrically ($\lambda$=405 nm). Human AADC expression as a function of vector input is fitted using a spline curve (SigmaPlot). The AAV2-AADC reference vector is measured concurrently with the test sample.

While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

All publications, patents and patent applications referred to herein are hereby incorporated by reference in their entireties.

We claim:

1. A composition for the storage of purified, recombinant adeno-associated virus (AAV) vector particles, comprising:
   purified, recombinant AAV vector particles at a concentration exceeding $1 \times 10^{13}$ vg/ml up to $6.4 \times 10^{13}$ vg/ml;
   a pH buffer, wherein the pH of the composition is between 7.5 and 8.0; and
   excipients comprising one or more multivalent ions selected from the group consisting of citrate, sulfate, magnesium, and phosphate; wherein the ionic strength of the composition is greater than 200 mM, and wherein the purified AAV vector particles are stored in the composition without significant aggregation.

2. The composition of claim 1, further comprising ethylene oxide/propylene oxide block copolymer Pluronic® F68.

3. The composition of claim 2, wherein the Pluronic® F68 is present at a concentration of 0.001% (w/v).

4. The composition of claim 1, wherein the pH buffer is 10 mM Tris, pH 8.0 and the excipients comprise 100 mM sodium citrate.

5. The composition of claim 1, wherein the purified, recombinant AAV vector particles have an average particle radius (Rh) of less than about 20 nm as measured by dynamic light scattering.

6. The composition of claim 1, wherein recovery of the purified, recombinant virus particles is at least about 90% following filtration of the composition of said AAV vector particles through a 0.22 μm filter.

* * * * *